United States Patent
Dutt et al.

(10) Patent No.: US 10,717,727 B2
(45) Date of Patent: *Jul. 21, 2020

(54) PYRIDINIUM COMPOUNDS

(71) Applicant: TORRENT PHARMACEUTICALS LIMITED, Ahmedabad (IN)

(72) Inventors: Chaitanya Dutt, Gandhinagar (IN); Rameshchandra Gupta, Gandhinagar (IN); Manish Patel, Gandhinagar (IN); Jaya Abraham, Gandhinagar (IN); Vivek Mishra, Gandhinagar (IN); Amit Kesarwani, Gandhinagar (IN); Shailesh Deshpande, Gandhinagar (IN); Shital Kumar Zambad, Gandhinagar (IN); Anoop Mathur, Gandhinagar (IN); Jignesh Kotecha, Gandhinagar (IN); Sachin Latad, Gandhinagar (IN); Anita Chaudhari, Gandhinagar (IN)

(73) Assignee: Torrent Pharmaceuticals Limited, Gujarat, Ahmedabad (IN)

( * ) Notice: Subject to any disclaimer, the term of this patent is extended or adjusted under 35 U.S.C. 154(b) by 0 days.

This patent is subject to a terminal disclaimer.

(21) Appl. No.: 16/267,224

(22) Filed: Feb. 4, 2019

(65) Prior Publication Data

US 2019/0169175 A1 Jun. 6, 2019

Related U.S. Application Data

(62) Division of application No. 15/564,715, filed as application No. PCT/IB2016/051917 on Apr. 5, 2016, now Pat. No. 10,233,175.

(30) Foreign Application Priority Data

Apr. 8, 2015 (IN) .......................... 1473/MUM/2015

(51) Int. Cl.
*C07D 409/06* (2006.01)
*C07C 53/126* (2006.01)
*A61P 25/00* (2006.01)
*A61K 31/4436* (2006.01)
*A61K 45/06* (2006.01)

(52) U.S. Cl.
CPC ........ *C07D 409/06* (2013.01); *A61K 31/4436* (2013.01); *A61K 45/06* (2013.01); *A61P 25/00* (2018.01); *C07C 53/126* (2013.01)

(58) Field of Classification Search
CPC .......................... C07D 409/06; A61K 31/4436
See application file for complete search history.

(56) References Cited

U.S. PATENT DOCUMENTS

| | | | |
|---|---|---|---|
| 6,462,057 B1 | 10/2002 | Sankaranarayanan | |
| 6,608,094 B2 | 8/2003 | Sankaranarayanan | |
| 6,624,178 B2 | 9/2003 | Sankaranarayanan | |
| 10,233,175 B2 * | 3/2019 | Dutt ........................ | A61P 25/00 |

FOREIGN PATENT DOCUMENTS

| | | |
|---|---|---|
| EP | 1222171 | 7/2002 |
| WO | 01/25208 | 4/2001 |

OTHER PUBLICATIONS

International Search Report for corresponding Application No. PCT/IB2016/051917 dated Jul. 8, 2016.

* cited by examiner

*Primary Examiner* — Golam M Shameem
(74) *Attorney, Agent, or Firm* — Melissa M. Hayworth; E. Joseph Gess; Daniel R. Evans

(57) ABSTRACT

The present invention relates to novel pyridinium compounds, their isomers, steroisomers, atropisomers, conformers, tautomers, polymorphs, hydrates and solvates. The present invention also encompasses process for preparing novel compounds and pharmaceutical composition of said compounds. The invention further relates to the use of the above mentioned compounds for the preparation of medicament for use as pharmaceuticals.

8 Claims, 1 Drawing Sheet

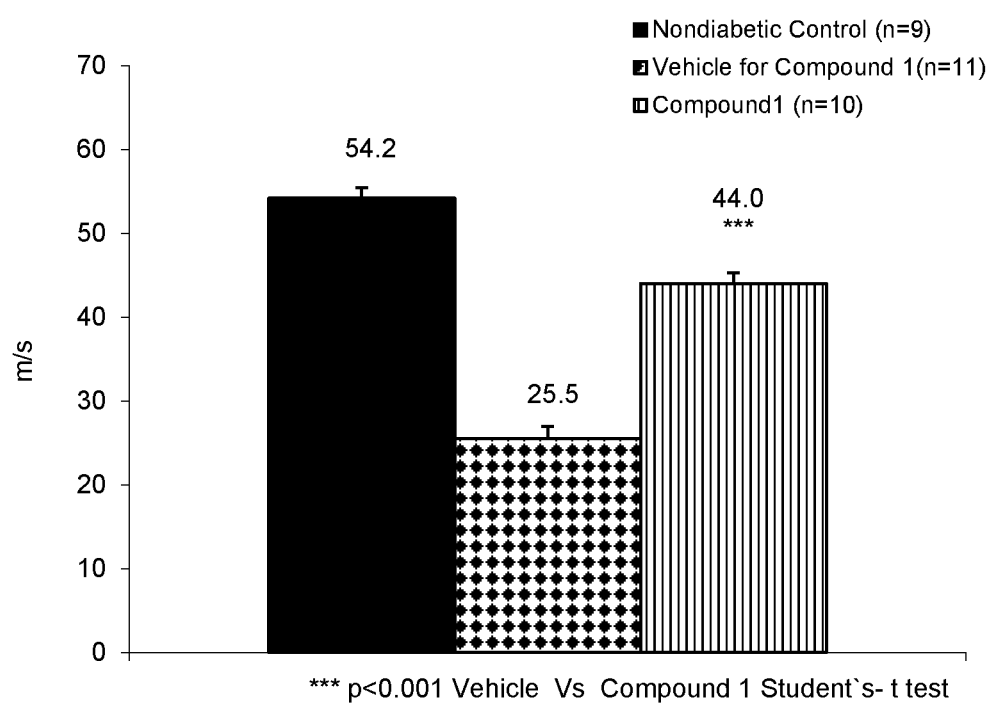

PYRIDINIUM COMPOUNDS

PRIOR APPLICATIONS

The present application is a divisional of U.S. application Ser. No. 15/564,715 filed Oct. 5, 2017 entitled "Novel Pyridinium Compounds", which is national stage filing under 35 U.S.C. 371 of PCT/IB2016/051917 filed Apr. 5, 2016, entitled "Novel Pyridinium Compounds", the contents of both of which are incorporated herein by reference in their entireties.

FIELD OF THE INVENTION

The present invention relates to novel pyridinium compounds, their isomers, steroisomers, atropisomers, conformers, tautomers, polymorphs, hydrates and solvates. The present invention also encompasses process for preparing novel compounds and pharmaceutical composition of said compounds. The invention further relates to the use of the above mentioned compounds for the preparation of medicament for use as pharmaceuticals.

BACKGROUND OF THE INVENTION

Advanced glycation end products (AGEs) are formed by a complex chain of reactions between reducing sugar such as glucose with proteins, resulting in the formation of multimeric complexes that trigger several pathological events (Pathak et al; *Eur J Med Res* (2008) 13: 388-398).

Advanced glycation end products (AGEs) have been implicated in the pathogenesis of a variety of debilitating diseases such as complications of diabetes, atherosclerosis, Alzheimer's and Rheumatoid arthritis, as well as in the normal aging process. In diabetes, where blood glucose level is significantly higher than normal, the reaction of glucose with several proteins such as haemoglobin and collagen, gives rise to the formation of AGE, which in turn, is responsible for the complications associated with diabetes, such as nephropathy, neuropathy, microangiopathy, endothelial dysfunction and other organ dysfunctions. In addition, the activity of several growth factors, such as basic fibroblast growth factor, is also impaired. AGE products, unlike normal proteins in tissue, have a slower rate of turnover and replenishment. It has been reported that AGE products may in fact elicit a complex immunological reaction involving RAGE (Receptor for Advanced Glycation End Products) and activation of several incompletely defined immunological processes. It has been documented that diabetes with evidence of microangiopathy and macroangiopathy also show evidence of oxidative stress, the mechanism of which has not been elucidated. (Stehouwer et al; *Cardiovascular Research* 1997; 34:55-68 and Smit et al.; *Current Medicinal Chemistry* 2004; 11:2767-84). Due to the clinical significance of AGE formation, several successful therapeutic approaches have been tried based upon intervening in the accumulation of AGEs. One of the approaches is to inhibit the formation of AGEs from its precursors, by the administration of therapeutic agents. In another approach for controlling levels of AGEs in tissues, therapeutic agent is administered which can reverse or break AGE cross-links, especially in those tissues in which AGE cross-links have already accumulated to levels which are responsible for subclinical or clinical pathology.

EP1243581, EP1222171 and EP1373263 describe pyridinium derivatives as AGE inhibitor or AGE breaker for management of complications associated with diabetes and aging related disorders.

Joline et al discloses pyridoxamine class of compounds as AGE inhibitors for treatment of diabetic nephropathy, and concluded that pyridoxamine compounds should be tested for safety profile when used for treatment of diabetes. (*J Am Soc Nephrol* 2012; 3: 6-8)

Though prior art provides various AGE inhibitor and the compounds having dual activity including AGE inhibition and AGE breaking; none of the AGE specific molecule has yet been reached to advanced clinical stage. There exists a need of new therapeutic molecules which are safe and effective in treating and controlling various pathologies caused due to formation and accumulation of AGE.

Present invention provides novel pyridinium compounds as AGE inhibitor and AGE breaker, which have demonstrated improved efficacy with desired safety profile.

SUMMARY OF THE INVENTION

In one embodiment, the present invention provides novel compounds of formula (I), (I)

[Structure of formula (I): a pyridinium ring with $R^1$ substituent, a carboxamide group $-C(O)-NH-NH-R^2$ at 3-position, $Y^-$ counter-ion, and N-substituent $-CH_2-C(O)-R^3$, with $\cdot nY$]

and isomers, stereoisomers, atropisomers, conformers, tautomers, polymorphs, hydrates and solvates thereof;
wherein;
$Y^-$ is anion of Y
Y is selected from nitric acid, $(C_2\text{-}C_{12})$alkyl sulfonic acid, $(C_3\text{-}C_{12})$cycloalkyl sulfonic acid, primary bile acids, secondary bile acids, conjugated bile acids, $CH_3-(CH_2)_z-COOH$, branched $(C_4\text{-}C_{14})$alkanecarboxylic acid, $(C_4\text{-}C_{14})$alkenecarboxylic acid, $(C_4\text{-}C_{14})$alkynecarboxylic acid and $C_3\text{-}C_{12}$ cycloalkanecarboxylic acid;
Z is selected from 1 to 14;
n is selected from 0 to 5;
$R^1$ is independently selected from hydrogen, $(C_1\text{-}C_8)$ alkyl, $(C_1\text{-}C_8)$ perhaloalkyl, $(C_3\text{-}C_8)$cycloalkyl, hetero$(C_3\text{-}C_{14})$cycloalkyl, aryl, aryl$(C_1\text{-}C_8)$alkyl, heteroaryl, heteroaryl$(C_1\text{-}C_8)$alkyl, $(C_1\text{-}C_8)$alkoxy, carboxamido, $-NHCO-(C_1\text{-}C_8)$alkyl, $-NR^5R^6$, acyl, acyloxy, $(C_1\text{-}C_8)$ alkoxycarbonyl, sulfonamido, halo, cyano, and nitro;
$R^2$ is selected from $R^4$, $-C(O)R^4$, $-C(O)NHR^4$, $-SO_2R^4$, $-C(O)NR^5R^6$ or structure A(I);

A(I)

[Structure A(I): pyridinium ring with $R^1$ substituent, acetyl group at 3-position, and N-substituent $-CH_2-C(O)-R^3$]

$R^3$ is independently selected from $(C_1\text{-}C_8)$alkyl, $(C_1\text{-}C_8)$ perhaloalkyl, $(C_3\text{-}C_8)$cycloalkyl, hetero$(C_3\text{-}C_{14})$cycloalkyl, aryl, aryl$(C_1\text{-}C_8)$alkyl, heteroaryl, heteroaryl$(C_1\text{-}C_8)$alkyl, $(C_1\text{-}C_8)$alkoxy, aryloxy, amino, —$NR^5R^6$, —$NHR^4$, acyloxy and sulfonamide; $R^4$ is selected from $(C_1\text{-}C_8)$alkyl, $(C_1\text{-}C_8)$ perhaloalkyl, $(C_3\text{-}C_8)$cycloalkyl, hetero$(C_3\text{-}C_{14})$cycloalkyl, aryl, aryl$(C_1\text{-}C_8)$alkyl and heteroaryl;

$R^5$ and $R^6$ are independently selected from hydrogen, $(C_1\text{-}C_8)$alkyl, $(C_3\text{-}C_8)$cycloalkyl, aryl, aryl$(C_1\text{-}C_8)$alkyl and heteroaryl or $R^5$ and $R^6$ may together form a 4-8 membered saturated or unsaturated monocyclic or bicyclic ring, may be fused with benzene which may optionally contain one to two heteroatoms, selected from O, N and S.

In another embodiment, the present invention provides a method for preparation of a compound of formula (I) as herein described in Schemes 1 to 3.

In another embodiment, the present invention provides a pharmaceutical composition comprising a compound of formula (I), optionally in admixture with a pharmaceutically acceptable excipient, adjuvant or carrier.

In another embodiment, present invention provides a method for treating disease condition selected from diabetes and aging related macrovascular and microvascular complications including heart failure, nephrological disorder, neuropathy, atherosclerosis, retinal disorder; dermatological disorder; endothelial or other organ dysfunction and growth impairment by administering a therapeutically effective amount of a compound of formula (I) to a mammal in need thereof.

Another embodiment of the present invention is the use of a compound of formula (I) for the preparation of a medicament for treating disease condition selected from diabetes and aging related macrovascular and microvascular complications including heart failure, nephrological disorder, neuropathy, atherosclerosis, retinal disorder; dermatological disorder; endothelial or other organ dysfunction and growth impairment.

Another embodiment of present invention provides pharmaceutical combination comprising compound of formula (I) and one or more therapeutic agent selected from a) antihypertensive agent; b) hypolipidemic agent; c) antidiabetic agent; d) antiplatelet agent; e) anti-thrombotic agent; f) antiobesity agent; g) agent for treatment of heart failure; and h) drug for diabetic vascular complications; i) agents for cardiovascular risk reduction; or a pharmaceutically acceptable salts thereof.

Another embodiment of present invention provides a method for treating disease condition selected from diabetes and aging related macrovascular and microvascular complications including heart failure, nephrological disorder, neuropathy, atherosclerosis, retinal disorder; dermatological disorder; endothelial or other organ dysfunction and growth impairment by administering a therapeutically effective amount of a compound of formula (I) and one or more therapeutic agent selected from a) antihypertensive agent; b) hypolipidemic agent; c) antidiabetic agent; d) antiplatelet agent; e) anti-thrombotic agent; f) antiobesity agent; g) agent for treatment of heart failure; and h) drug for diabetic vascular complications; i) agents for cardiovascular risk reduction; or a pharmaceutically acceptable salts thereof.

Another embodiment of present invention provides use of a compound of formula (I) and one or more therapeutic agent selected from a) antihypertensive agent; b) hypolipidemic agent; c) antidiabetic agent; d) antiplatelet agent; e) anti-thrombotic agent; f) antiobesity agent; g) agent for treatment of heart failure; and h) drug for diabetic vascular complications; i) agents for cardiovascular risk reduction; or a pharmaceutically acceptable salts thereof, for the preparation of a medicament for treating disease condition selected from diabetes and aging related macrovascular and microvascular complications including heart failure, nephrological disorder, neuropathy, atherosclerosis, retinal disorder; dermatological disorder; endothelial or other organ dysfunction and growth impairment.

DESCRIPTION OF FIGURE

FIG. 1: Effect of Compound 1 on Nerve Conduction Velocity (NCV) in Diabetic rats

DETAILED DESCRIPTION OF THE INVENTION

In one embodiment, the present invention provides novel compounds of formula (I),

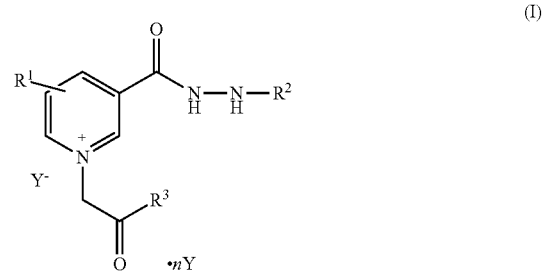

and isomers, stereoisomers, atropisomers, conformers, tautomers, polymorphs, hydrates and solvates thereof, wherein Y, Y$^-$, n, R$^1$, R$^2$ and R$^3$ are as defined above.

In a preferred embodiment, the present invention provides novel compounds of formula (I), wherein Y is $CH_3$—$(CH_2)_z$—COOH, Y$^-$ is $CH_3$—$(CH_2)_z$—COO$^-$, and Z, n, R$^1$, R$^2$ and R$^3$, are as defined above.

In another preferred embodiment, the present invention provides novel compounds of formula (I), wherein n is 1-3, most preferably n is Y, Y$^-$, Z, R$^1$, R$^2$ and R$^3$, are as defined above.

In a preferred embodiment, the present invention provides novel compounds of formula (II), (II)

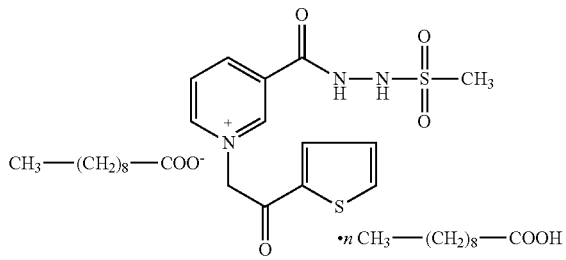

wherein n is 1 to 3, more preferably n is 1 to 2, most preferably, n is 1.

It was surprisingly noted that when n is more than 0, preferably 1-3, more preferably 1-2; most preferably 1, it increases therapeutic efficacy of the compounds.

A family of specific compounds of particular interest within the above formula (I) consists of compound as follows:

| Compd. No. | Chemical Structure |
|---|---|
| 1 | 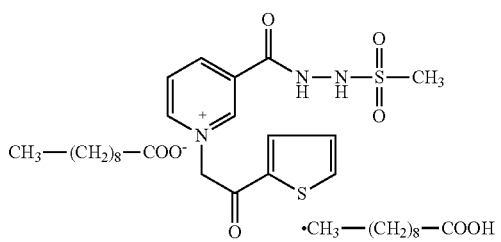 |
| 2 | 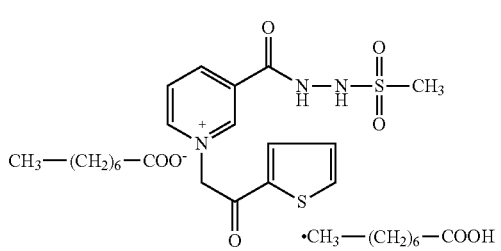 |

Definitions

The following definitions apply to the terms as used throughout this specification, unless otherwise limited in specific instances:

The term "compound" employed herein refers to any compound encompassed by the generic formula disclosed herein. The compounds described herein may contain one or more double bonds and therefore, may exist as isomers, stereoisomers, such as geometric isomers, E and Z isomers, and may possess asymmetric carbon atoms (optical centers) and therefore may exist as enantiomers or diastereoisomers. Accordingly, the chemical structures described herein encompasses all possible stereoisomers of the illustrated compounds including the stereoisomerically pure form (e.g., geometrically pure) and stereoisomeric mixtures (racemates). The compound described herein, may exist as a conformational isomers such as chair or boat form. The compound described herein may also exist as atropisomers. The compounds may also exist in several tautomeric forms including the enol form, the keto form and mixtures thereof. Accordingly, the chemical structures described herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds of the invention include, but are not limited to $^2H$, $^3H$, $^{13}C$, $^{14}C$, $^{15}N$, $^{18}O$, $^{17}O$ etc. Compounds may exist in unsolvated forms as well as solvated forms, including hydrated forms. In general, compounds may be hydrated or solvated. Certain compounds may exist in multiple crystalline or amorphous forms. In general, all physical forms are equivalent for the uses contemplated herein and are intended to be within the scope of the present invention.

The use of the terms "a" & "an" & "the" and similar referents in the context of describing the invention (especially in the context of the following claims) are to be construed to cover both the singular and the plural, unless otherwise indicated herein or clearly contradicted by context.

As used herein, the term "polymorph" pertains to compounds having the same chemical formula, the same salt type and having the same form of hydrate/solvate but having different crystallographic properties.

As used herein, the term "hydrate" pertains to a compound having a number of water molecules bonded to the compound.

As used herein, the term "solvate" pertains to a compound having a number of solvent molecules bonded to the compound.

The term "substituted", as used herein, includes mono- and poly-substitution by a named substituent to the extent such single and multiple substitution (including multiple substitution at the same site) is chemically allowed and which means that any one or more hydrogens on the designated atom is replaced with a selection from the indicated group, provided that the designated atom's normal valence is not exceeded, and that the substitution results in a stable compound, for example, when a substituent is keto, then the two hydrogens on the atom are replaced. All substituents ($R_1$, $R_2$ . . . ) and their further substituents described herein may be attached to the main structure at any heteroatom or carbon atom which results in formation of stable compound.

The term "alkyl" used either alone or in attachment with another group refers to an optionally substituted saturated aliphatic hydrocarbon radical having the carbon atoms as denoted by carbon numbers. For example, $(C_1-C_8)$alkyl denotes alkyl group having carbon atoms selected from 1 to 8. Said "alkyl" is straight chain for example, methyl, ethyl, n-propyl, n-butyl, n-pentyl, n-hexyl, n-heptyl, n-octyl or branched chain and it may contain one or more double or triple bonds. When said alkyl contains one or more double bond or triple bond, it is referred as "alkene" and alkyne respectively. The said alkyl may also contain $(C_3-C_6)$cycloalkyl ring in a spiro manner. Said alkyl, alkene and alkyne may be optionally substituted with halo, cyano, nitro, $(C_1-C_8)$perhaloalkyl, $(C_1-C_8)$alkyl, aryl, cyclo$(C_3-C_8)$alkyl, hetero$(C_3-C_{14})$cycloalkyl or aryl$(C_1-C_8)$alkyl.

The term "alkoxy" used either alone or in attachment with another group refers to any alkyl group as defined herein above attached to the parent molecular moiety through an oxygen bridge, having the carbon atoms as denoted by carbon numbers. For example $(C_1-C_8)$ alkoxy denotes alkyl group having 1-8 carbon atoms attached through oxygen bridge. Said alkoxy includes methoxy, ethoxy, n-propoxy, isopropoxy, n-butoxy, isobutoxy, sec-butoxy, tert-butoxy and straight and branched chained pentoxy, hexoxy, heptoxy and octoxy.

The term "cycloalkyl" used either alone or in attachment with another group refers to an optionally substituted a fully or partially saturated cyclic ring system having carbon atoms as denoted by carbon numbers. For example, $(C_3-C_8)$cycloalkyl denotes cycloalkyl group having carbon atoms selected from 3 to 8. The said "cycloalkyl" means a cyclic ring system containing only carbon atom in the ring system backbone such as cyclopropyl, cyclobutyl, cyclopentyl, cyclohexyl, cycloheptyl and cyclooctyl. Cycloalkyl may have any degree of saturation provided that at least one ring in the ring system is not aromatic.

The term "aryl" refers to an aromatic group for example, which is a 6 to 10 membered monocyclic or bicyclic carbon-containing ring system. The aryl groups include, but are not limited to, phenyl, naphthyl, biphenyl, tetrahydronaphthyl and indanyl. Preferably, aryl is phenyl, indanyl or naphthyl. Said aryl may be mono or disubstituted with hydrogen, halogen, $(C_1-C_8)$alkyl, $(C_1-C_8)$alkoxy, nitro, cyano, —OH or trifluoromethyl.

The term "heteroaryl" refers to an aromatic group for example, which is a 5 to 14 membered monocyclic or bicyclic ring system, which has at least one heteroatom. The term "heteroatom" as used herein includes O, N, S, wherein n is as defined above. In bicyclic ring system, ring can be fused through a bridge heteroatom. The heteroaryl groups include, but are not limited to pyrrolyl, furanyl (furyl), thiophenyl (thienyl), pyrazolyl, imidazolyl, oxazolyl, isoxazolyl, thiazolyl, triazolyl, oxadiazolyl, thiadiazolyl, tetrazolyl, pyridinyl (pyridyl), pyridazinyl, pyrimdinyl, pyrazinyl, triazinyl, indolyl, benzofuranyl, benzothiophenyl (benzothienyl), indazolyl, benzimidazolyl, benzoxazolyl, benzisoxazolyl, benzothiazolyl, quinolinyl, isoquinolinyl, cinnolinyl, quinazolinyl, quinoxalinyl, phthalazinyl or naphthyridinyl. Said heteroaryl may be mono or disubstituted with hydrogen, halogen, $(C_1-C_8)$alkyl, $(C_1-C_8)$alkoxy, nitro, cyano, —OH or trifluoromethyl.

The term "hetero$(C_3-C_{14})$cycloalkyl" refers to a fully or partially saturated cyclic group, for example, which is a 3 to 14 membered monocyclic or bicyclic ring system, which has at least one heteroatom. The term "heteroatom" as used herein includes O, N, S. In bicyclic heterocyclic system, at least one ring is not aromatic and the rings can also be attached to each other in a spiro manner. Said hetero$(C_3-C_{14})$cycloalkyl may be mono or disubstituted with hydrogen, halogen, $(C_1-C_8)$alkyl, $(C_1-C_8)$alkoxy, nitro, cyano, —OH or trifluoromethyl.

As used herein, "room temperature" or "RT" refers to a temperature between 20° C. and 35° C.

As used herein, the term "mammal" means a human or an animal such as monkeys, primates, dogs, cats, horses, cows, etc.

The terms "treating" or "treatment" of any disease or disorder as used herein to mean administering a compound to a mammal in need thereof. The compound may be administered thereby providing a prophylactic effect in terms of completely or partially preventing or delaying the onset of a disease or disorder or sign or symptom thereof; and/or the compound may be administered thereby providing a partial or complete cure for a disease or disorder and/or adverse effect attributable to the disorder.

The phrase "a therapeutically effective amount" means the amount of a compound that, when administered to a patient for treating, preventing or managing a disease, is sufficient to effect such treatment, prevention or management for the disease. The "therapeutically effective amount" will vary depending on the compound, mode of administration, the disease and its severity and the age, weight, etc., of the patient to be treated.

Throughout this specification and the appended claims it is to be understood that the words "comprise" "has" and "include" and variations such as "comprises", "comprising", "having", "includes", "including" are to be interpreted inclusively, unless the context requires otherwise. That is, the use of these words may imply the inclusion of an element or elements not specifically recited.

In another embodiment, present invention provides the process for preparing the compounds of formula (I).

The following reaction schemes are given to disclose the synthesis of the compounds according to the present invention.

Accordingly, the compounds of formula (I) of the present invention may be prepared as described in the schemes below.

SCHEME-1

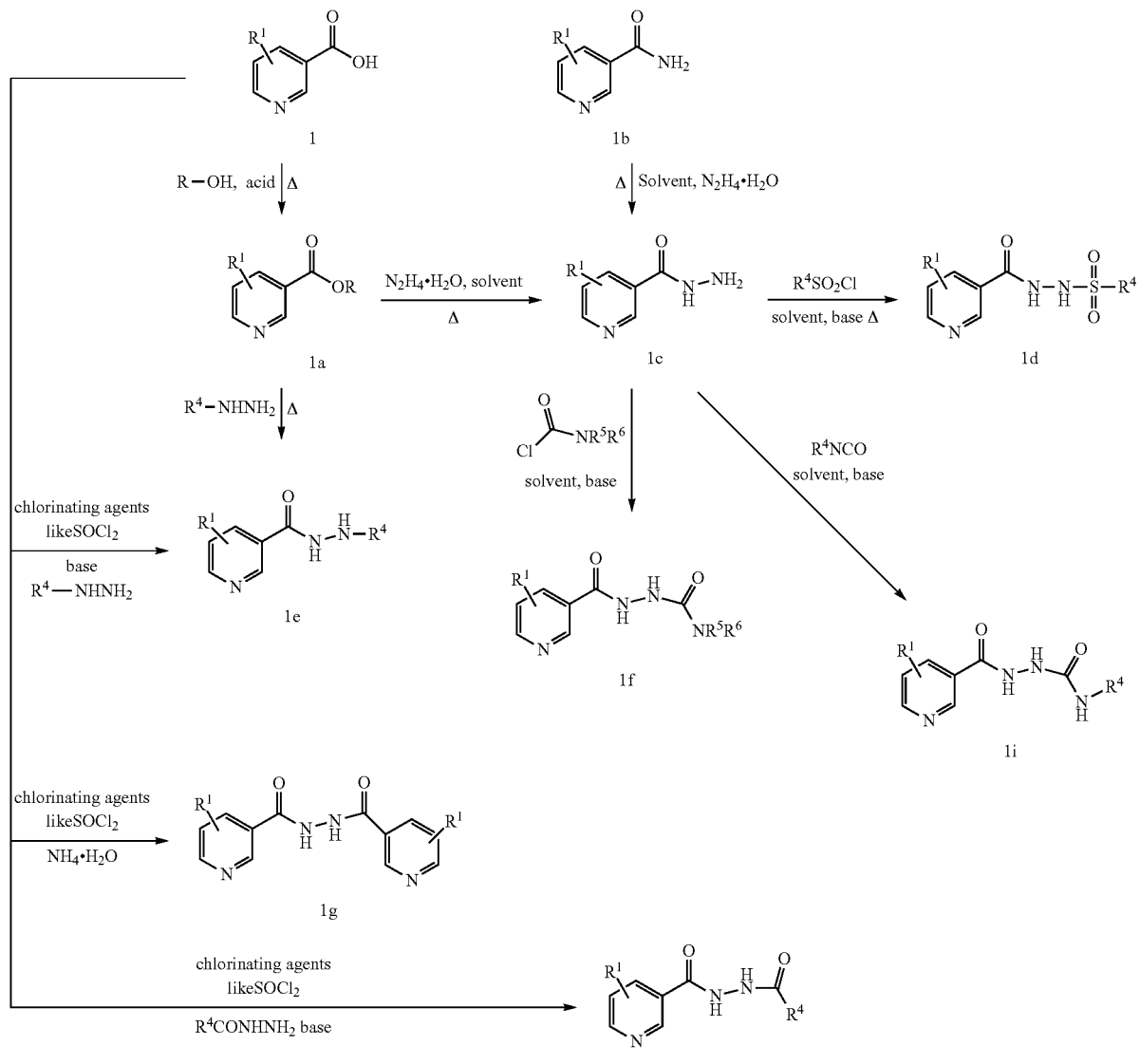

Scheme 1: $R^1$, $R^2$, $R^4$, $R^5$ and $R^6$ are same as defined above for compound of formula (I) and R is $(C_1-C_6)$alkyl.

Compound of formula (1a) as shown in scheme-1 can be prepared by refluxing a mixture of (1), suitable alcohol and mineral acid such as hydrochloric acid, sulphuric acid, hydrobromic acid more preferably with sulphuric acid.

Compound of formula (1c) can be prepared by refluxing a solution of compounds of formula (1a) or compound of formula (1b) with hydrazine hydrate in aprotic or protic solvent such as acetonitrile, tetrahydrofuran, isopropyl alcohol, ethanol, methanol and the like, preferably isopropyl alcohol and acetonitrile or nonpolar solvent such as toluene or combination thereof.

Compound of formula (1d) can be prepared by reacting compounds (1c) with suitable sulfonyl chloride in presence of aprotic solvent such as tetrahydrofuran, acetonitrile, ethyl acetate, methylene chloride, preferably tetrahydrofuran and organic or inorganic base such as pyridine, triethylamine, diisopropyl ethylamine, sodium carbonate, sodium bicarbonate and the like.

Compound of formula (1e) can be prepared by reacting compound (1) with chlorinating agent such as thionyl chloride, oxalyl chloride, phosphorus penta chloride, phosphorous oxy chloride, phosphorous tri chloride, sulphuryl chloride more preferably thionyl chloride, optionally in presence of solvent such as toluene, methylene chloride, ethyl acetate, tetrahydrofuran, 1,4 dioxane and the like, to provide corresponding acid chloride followed by reaction with substituted hydrazine in presence of suitable base such as pyridine, triethylamine, diisopropyl ethylamine, sodium carbonate, sodium bicarbonate, potassium carbonate and the like.

Alternatively, compound of formula (1e) can be prepared by reacting substituted hydrazine derivatives with compound (1a), optionally in the presence of protic or aprotic solvent such as tetrahydrofuran, acetonitrile, ethyl acetate, methanol, ethanol, isopropyl alcohol, dimethyl formamide & the like.

Compound of formula (1f) can be prepared by reacting compound (1c) with suitable acid chloride in the presence of base such as pyridine, triethylamine, diisopropyl ethylamine, sodium carbonate, sodium bicarbonate, potassium carbonate & the like, and aprotic solvent such as tetrahydrofuran, acetonitrile, ethyl acetate, methylene chloride & the like.

Compound of formula (1g) can be prepared by reacting compound (1) with chlorinating agent such as thionyl chloride, oxalyl chloride, phosphorus penta chloride, phosphorous oxy chloride, phosphorous tri chloride, sulphuryl chloride more preferably thionyl chloride, optionally in the presence of solvent such as toluene, methylene chloride, ethyl acetate, tetrahydrofuran, 1,4 dioxane and the like, to provide corresponding acid chloride followed by reaction with hydrazine hydrate in the presence of base such as pyridine, triethylamine, diisopropyl ethylamine, hydrazine, sodium carbonate, sodium bicarbonate, potassium carbonate & the like and aprotic solvent such as tetrahydrofuran, acetonitrile, ethyl acetate, methylene chloride & the like.

Compound of formula (1h) can be prepared by reacting by reacting compound (1) with chlorinating agent such as thionyl chloride, oxalyl chloride, phosphorus penta chloride, phosphorous oxy chloride, phosphorous tri chloride, sulphuryl chloride more preferably thionyl chloride, optionally in the presence of solvent such as toluene, methylene chloride, ethyl acetate, tetrahydrofuran, 1,4 dioxane and the like, to provide corresponding acid chloride followed by reaction with substituted keto hydrazide in the presence of base such as pyridine, triethylamine, diisopropyl ethylamine, sodium carbonate, sodium bicarbonate, potassium carbonate & the like and aprotic solvent such as tetrahydrofuran, acetonitrile, ethyl acetate, methylene chloride & the like.

Compound of formula (1i) can be prepared by reacting by reacting compound (1c) with suitable isocynate, in the presence of solvent such as toluene, methylene chloride, ethyl acetate, tetrahydrofuran, acetonitrile, 1,4 dioxane and the like, and base such as pyridine, triethylamine, diisopropyl ethylamine, sodium carbonate, sodium bicarbonate, potassium carbonate & the like.

SCHEME-2

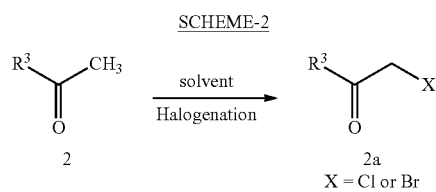

Scheme-2: $R^3$ is same as defined above for compound of formula (I).

Compound of formula (2a) can be prepared by acid catalyzed halogenations of substituted acetyl (2) in aprotic solvent such as but not limited to tetrahydrofuran, acetonitrile, ethyl acetate, methylene chloride more preferably ethyl acetate and methylene chloride using appropriate halogenations reagent such as bromine, chlorine, thionyl chloride, sulphuryl chloride, hydrobromic acid, more preferably sulphuryl chloride and bromine.

Compound (3) can be prepared by heating compounds of formula (1d) or (1e) or (1f) or (1g) or (1h) or (1i) as shown in scheme-1 with compounds of formula (2a) as shown in scheme-2 in the presence of protic or aprotic solvent such as isopropyl alcohol, ethanol, methanol, dimethyl formamide, dimethyl sulfoxide and the like.

Compound of formula (I) can be prepared by reacting compound (3) with sodium salt of acid Y in protic or aprotic solvent such as water, methanol and the like or by reacting compound (3) with acid Y in the presence of polar protic or aprotic solvent such as water and inorganic base such as sodium carbonate, sodium bicarbonate, sodium hydroxide, potassium hydroxide and the like, more preferably sodium hydroxide. Alternatively, compounds (3) is reacted with inorganic base such as sodium carbonate, sodium bicarbonate, sodium hydroxide, potassium hydroxide & the like or organic base such as triethylamine and the like, more preferably sodium bicarbonate in polar protic or aprotic solvent such as water to give compound (3a), which is then isolated and reacted with acid Y optionally, in the presence of protic or aprotic solvent such as water, methanol, isopropyl alcohol, tetrahydrofuran and the like to give compound of formula (I).

SCHEME-3

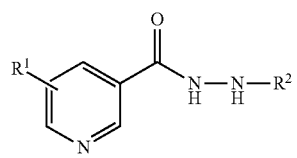

1d or 1e or 1f or 1g or 1h or 1i

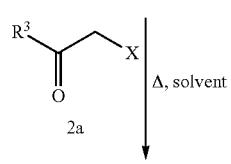

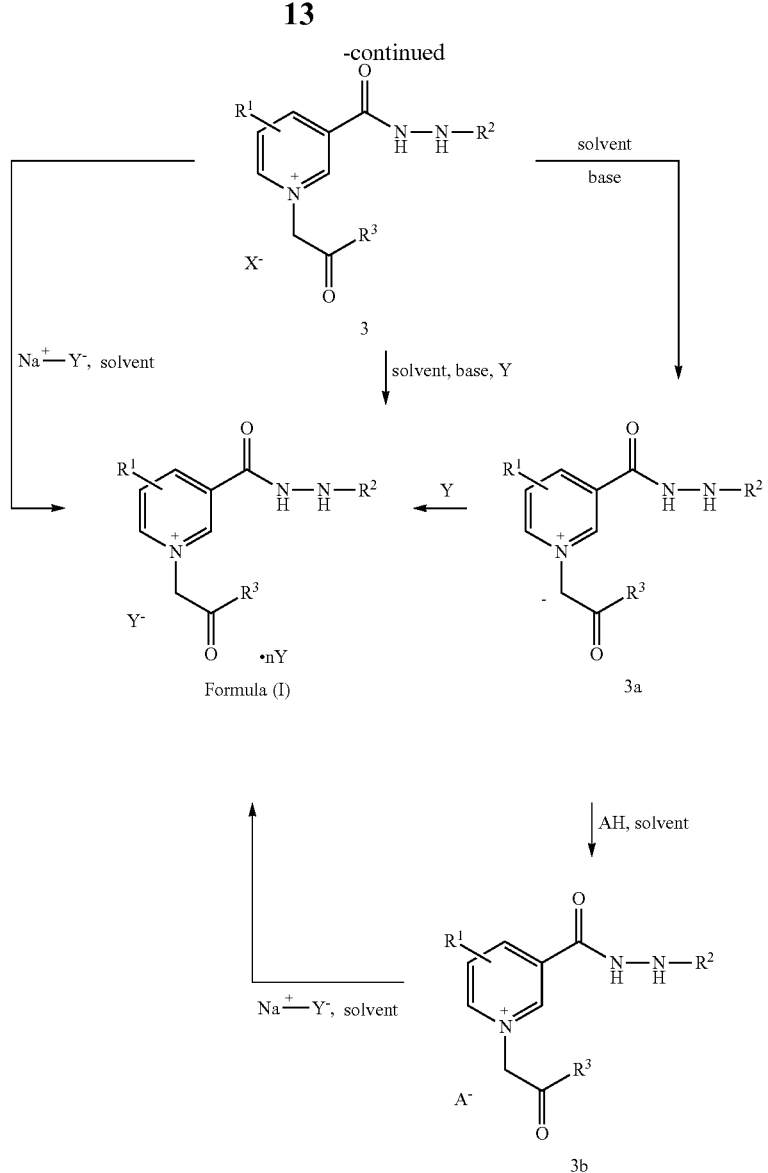

Scheme 3: $R_1$, $R^2$, $R^3$, Y and Y⁻ are same as defined for compounds of formula (I); X is halide and X⁻ is anion of halide;

Further Compound of formula (I) can be prepared from reacting compound (3b) with sodium salt of acid Y in protic or aprotic solvent such as water, methanol and the like. Compound (3b) can be prepared from (3a) in protic or aprotic solvent such as water, methanol or mixture thereof using various acid (AH) where A⁻ are counter ion selected from alkylsulphonate, arylsulphonate, heteroaryl sulfonate, sulphate, hydrogen sulphate perchlorate, oxalate, trifluoroactate, acetate, tartrate, malonate, succinate, maleate, fumarate, adipate, glutamate, glycolate, lactate, pyruvate, suberate, malate, citrate, nitrate, aryl carboxylate, heteroaryl carboxylate, cinnamate, phthalate, mandelate and the like.

Alternatively, compound (3b) can be converted to compound (3a) in presence of suitable base and solvent which upon addition of acid Y gives the compounds of formula (I).

Alternative to the given schemes, one of ordinary skill will readily synthesize the compounds according to the present invention using conventional synthetic organic techniques from suitable starting material which are either commercially available or may be readily prepared.

One embodiment of present invention provides process of preparation of compound of formula (I) comprising of reacting compound of formula (3)

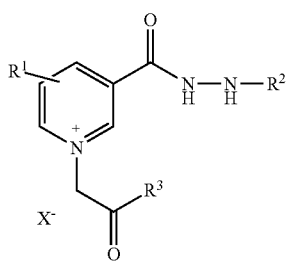

Or compound of formula (3b)

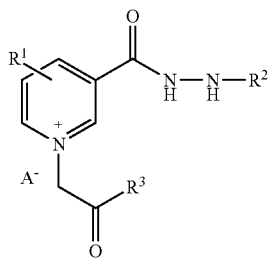

with Y or its pharmaceutically acceptable salt, in presence of solvent or base or mixture thereof;
wherein, $R^1$, $R^2$, $R^3$, Y and $A^-$ are as defined above, and X is halide.

In another embodiment of present invention provides process of preparation of compound of formula (I) comprising of reacting compound of formula (3a)

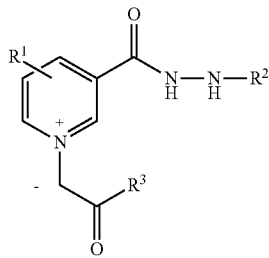

with Y, or its pharmaceutically acceptable salt, optionally in presence of solvent or base or mixture thereof wherein, $R^1$, $R^2$, $R^3$ and Y are as defined above.

A preferred embodiment of present invention provides process of preparation of compound of formula (II) comprising of reacting pharmaceutically acceptable salt of 3-{[2-(methylsulfonyl)hydrazinyl]carbonyl}-1-[2-oxo-2-(thiophen-2-yl)ethyl]pyridinium with $CH_3$—$(CH_2)_8$—COOH or its alkaline metal salt or alkaline earth metal salt, in presence of solvent and optionally in presence of base, wherein said pharmaceutically acceptable salts are selected from halide, alkylsulphonate, arylsulphonate, heteroaryl sulfonate, sulphate, hydrogen sulphate perchlorate, oxalate, trifluoroactate, acetate, tartrate, malonate, succinate, maleate, fumarate, adipate, glutamate, glycolate, lactate, pyruvate, suberate, malate, citrate, nitrate, aryl carboxylate, heteroaryl carboxylate, cinnamate, phthalate, mandelate and the like.

Said compound of formula (3), (3a), (3b) or pharmaceutically acceptable salt of 3-{[2-(methylsulfonyl)hydrazinyl] carbonyl}-1-[2-oxo-2-(thiophen-2-yl)ethyl]pyridinium are used in molar ratio of 6.0:0.5 to 0.5:6.0 with acid Y or its pharmaceutically acceptable salt such as alkaline metal salt or alkaline earth metal salt of $CH_3$—$(CH_2)_8$—COOH. Preferably, said molar ratio is 2.0:1.0 to 1.0:2.0. More particularly, 3-{[2-(methylsulfonyl)hydrazinyl]carbonyl}-1-[2-oxo-2-(thiophen-2-yl)ethyl]pyridinium chloride and $CH_3$—$(CH_2)_8$—COOH or its sodium salt are used in the molar ratio of 1.0:1.0.

Novel process according to present invention as described herein above preferably carried out in presence of one or more solvent. Said solvent can be selected from water, ethanol, methanol, isopropyl alcohol, acetone, acetonitrile, dioxane, dimethylformamide, methylene chloride, chloroform, dichloromethane, ether or mixture thereof. Preferably, polar solvent is used such as water or its mixture with other polar solvents such as methanol. Additionally, compound of formula (I) or (II) may be subjected to washing with non-polar solvent such as heptane, hexanes or toluene; more preferably heptane.

Wherever employed, base is selected from organic or inorganic base such as sodium carbonate, sodium bicarbonate, sodium hydroxide, potassium carbonate, potassium bicarbonate, potassium hydroxide, triethyl amine and pyridine.

Therefore, a preferred embodiment of present invention provides process of preparation of compound of formula (I) comprising of:
Reacting compound of formula

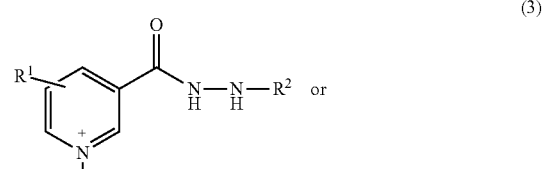

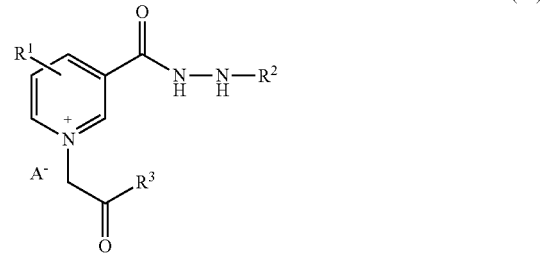

with Y or its pharmaceutically acceptable salt; in presence of solvent selected from water or mixture of water with polar or non-polar solvent;
wherein ratio of compound of formula (3) or (3b) to Y or its pharmaceutically acceptable salt ranges from 6.0:0.5 to 0.5:6.0;
and $R^1$, $R^2$, $R^3$, Y and $A^-$ are as defined above, and X is halide.

It was observed that when compound of formula 3, (3a) or (3b) are reacted with acid Y in presence of inorganic or organic base, to prepare compound of formula (I); the molar ratio of acid Y to inorganic/organic base has significant impact on isolation of compound of formula (I). In the process of preparation of compound of formula (I) according to the present invention, molar ratio of Y to inorganic/organic base used is 0.5:1.0 to 6.0:1.0. Preferably, said molar ratio is 1.0:1.0 to 2.0:1.0. More preferably, $CH_3$—$(CH_2)_8$—COOH and sodium hydroxide or triethylamine are used in the molar ratio of 1.0:1.0.

An alternate embodiment of present invention provides process of preparation of compound of formula (I) comprising of
a) reacting compound of formula selected from (1d), (1e), (1f), (1g), (1h) or (1i) with compound of formula (2a).
b) Adding Y or its pharmaceutically acceptable salt to the reaction mixture obtained in step a), optionally in presence of solvent or base or mixture thereof to give compound of formula (I).

Wherein compound (1d), (1e), (1f) (1g), (1h), (1i), (2a) and Y are as defined above.

Compound of formula (I) obtained according to any of the process according to present invention is subjected to drying. Drying process includes vacuum drying or air drying with or without heating. Preferably drying process is air drying by using fluid bed dryer. Drying of compound of formula I is used to obtain compound of formula I with water content of less than 5.0%, preferably less than 2.0%, most preferably less than 1.0% when measured using known techniques to calculate water, such as by KF. Surprisingly control of water content improves the flowability of compound of formula (I).

Thus, another embodiment of present invention provides a compound of formula I, wherein water by KF of said compound is less than 5.0%, preferably less than 2.0%, most preferably less than 1.0%.

Yet another embodiment of present invention provides a compound of formula I, wherein said compound is in anhydrate, monohydrate or dihydrate form. Preferably compound of formula I is in anhydrate form which is characterized by water content less than 2.0%, preferably, less than 1.0%, as measured by Karl Fischer Titration (KF) and 99.48° C.+/−2 to 103.22° C.+/−2 melting point as measured by Differential Scanning calorimetry (DSC).

It is within the purview of a person skilled in the art that variations in reaction time, temperature, solvents and/or reagents could increase the yields.

The compounds of the present invention may have chiral centers and occur as racemates, racemic mixtures and as individual diastereomers or enantiomers with all isomeric forms being included in the present invention. Therefore, where a compound is chiral, the separate enantiomers, substantially free of the other, are included within the scope of the invention; further included are all mixtures of the two enantiomers.

In present specification some general terms are used with their known intended meaning which are defined herein below:

| ESI | Electro spray ionization |
|---|---|
| APCI | Atmospheric pressure chemical ionization |

Mass of compounds prepared according to present invention is measured using Single quadrupole mass spectrometer (Water ZQ 2000 instrument) using APCI ionization technique (Electro spray chemical ionization Probe) or Finnigan LXQ, thermo instrument Technique using either ESI or APCI.

The novel compounds of the present invention were prepared according to the procedure of the schemes as described herein above, using appropriate materials and are further exemplified by the following specific examples. The examples are not to be considered or construed as limiting the scope of the invention set forth.

EXAMPLES FOR PREPARATION OF COMPOUNDS ACCORDING TO PRESENT INVENTION

Example 1: Preparation of Compound No 1

Step (a): Preparation of Methyl Nicotinate

To a stirred cold suspension of nicotinic acid (200 gm) in methanol (440 ml), Sulphuric acid (270 ml) was added slowly to control exothermicity. The reaction mixture was heated and stirred at 80-98° C. for 3 hrs. Reaction mixture was cooled to RT, quenched in ice cold water and neutralized with liquor ammonia. The neutralized solution was extracted with methylene chloride (1000 ml), dried over sodium sulphate and evaporated under vacuum to afford title compound as low melting light yellow to off white solid.

$^1$H NMR (DMSO-d$_6$, 400 MHz, ppm): 9.096-9.091 (1H, Singlet), 8.833-8.818 (1H, doublet), 8.32-8.29 (1H, doublet), 7.60-7.56 (1H, triplet), 3.29 (3H, Singlet)

Mass (m/z): 138 (M$^+$+1)

IR (KBr): 1727.1 cm$^{-1}$, 1289.3 cm$^{-1}$

Step (b): Preparation of Nicotinic Hydrazide

To a stirred solution of methyl nicotinate (500 gm) in isopropyl alcohol was added hydrazine hydrate (80%) (460 ml). Resultant mixture was heated and stirred at 80-85° C. for 4 hrs. Reaction mixture was cooled to RT. Separated solid was filtered, washed with isopropyl alcohol and dried to give title compound as off white solid.

Alternatively, title compound was prepared by adding hydrazine hydrate 80% (100 ml) in a stirred suspension of niacinamide (100 gm) in toluene, followed by heating and stirring at 80-90° C. for 10-15 hrs. Reaction mixture was cooled to 50-60° C. Tetrahydrofuran was added and reaction mixture was stirred at 40-45° C. for 2-3 hrs. Separated solid was filtered, suck dried and stirred in tetrahydrofuran at 40-45° C. for 1-2 hrs. Solid was filtered, washed with tetrahydrofuran and dried to afford nicotinic hydrazide as off white solid.

$^1$H NMR (DMSO-d$_6$, 400 MHz, ppm): 9.967 (1H, singlet), 8.967-8.961 (1H, singlet), 8.699-8.683 (1H, doublet), 8.167-8.138 (1H, doublet), 7.512-7.479 (1H, triplet), 4.567 (2H, Singlet)

Mass (m/z):138 (M$^+$+1)

IR (KBr): 3211.3 cm$^{-1}$, 1670.2 cm$^{-1}$

Step (c): Preparation of N'-(methylsulfonyl)pyridine-3-carbohydrazide

To a stirred suspension of nicotinic hydrazide (100 gm) in tetrahydrofuran (700 ml) was added pyridine (119 ml), followed by methane sulfonyl chloride (56.75 ml). Resultant suspension was refluxed for 4 hrs. Reaction mixture was cooled to RT and solid was filtered. Solid was recrystallized in water and dried to provide title compound as off white solid.

$^1$H NMR (DMSO-d$_6$, 400 MHz, ppm): 10.95 (1H, singlet), 9.74 (1H, singlet), 9.031-9.027 (1H, doublet), 8.744-8.759 (1H, doublet), 8.242-8.214 (1H, doublet), 7.517-7.539 (1H, triplet), 3.04 (1H, singlet)

Mass (m/z):214 (M$^+$+1)

IR (KBr): 3287.4 cm$^{-1}$, 1686.6 cm$^{-1}$, 1313.4 cm$^{-1}$

Step (d): Preparation of -2-chloro-1-(thiophen-2-yl) ethanone

To a stirred cold solution of 2-acetyl thiophene (100 gm) in ethyl acetate (900 ml) was added sulfuryl chloride (80 ml), which was diluted with ethyl acetate (100 ml) at 10-20° C. Reaction mass was stirred at RT for 1 hour and quenched in water. Organic layer was separated and washed with water followed by brine solution. Organic layer was dried over sodium sulphate and evaporated to afford liquid which was further purified by isopropyl: cyclohexane (1:10) to provide title compound as white to off white to powder.

¹H NMR (DMSO-d₆, 400 MHz, ppm): 8.10-8.11 (1H, dd), 8.04-8.05 (1H, dd), 7.28-7.30.027 (1H, dt), 5.09 (1H, singlet)

Mass (m/z): 161 (M⁺+1)

IR (KBr): 2990 cm⁻¹, 2945 cm⁻¹, 1674.57 cm⁻¹

Step (e): Preparation of 3-{[2-(methylsulfonyl)hydrazinyl]varbonyl}-1-[2-oxo-2-(thiophen-2-yl)ethyl]pyridinium chloride Suspension of N'-(methylsulfonyl)pyridine-3-carbohydrazide (100 gm) and 2-chloro-1-(thiophen-2-yl) ethanone (89.5 gm) in dimethyl formamide (500 ml) was heated and stirred at 85-90° C. for 15 hrs. Separated solid was filtered, washed with dimethyl formamide followed washing with ethyl acetate. Solid was refluxed in ethyl acetate, filtered and finally recrystallized from methanol and dried to provide title compound as white to off white solid.

¹H NMR (DMSO-d₆, 400 MHz, ppm): 11.57 (1H, singlet), 9.97 (1H, singlet), 9.58-9.027 (1H, singlet), 9.21-9.15 (2H, two doublets), 8.42 (1H, unresolved triplet), 8.24-8.27 (2H, unresolved multiplet), 7.43 (1H, triplet), 6.50 (2H, singlet), 3.11 (3H, singlet)

Mass (m/z): 340 (M⁺)

IR (KBr): 3319.3 cm⁻¹, 1713.6 cm⁻¹, 1672.2 cm⁻¹, 1336.6 cm⁻¹

Step (f): Compound No 1

(Method A)

To a stirred suspension of n-decanoic acid (45.8 gm) in water (600 ml) was added aqueous solution (400 ml) of sodium hydroxide (10.6 gm), followed by addition of aqueous solution (2000 ml) of 3-{[2-(methylsulfonyl)hydrazinyl]carbonyl}-1-[2-oxo-2-(thiophen-2-yl)ethyl]pyridinium chloride (100 gm) at RT and stirred for 1 hour. The separated solid was filtered, washed with water (600 ml) and dried to give title compound. The dried solid was stirred in n-heptane (275 ml) at 10-15° C. for 30 minutes, filtered, washed with n-heptane (55 ml) and dried to give title compound (41.0 gm) as solid.

(Method B)

To a stirred suspension of n-decanoic acid (4.58 gm) in methanol (100 ml) was added aqueous solution (20 ml) of sodium hydroxide (1.05 gm), followed by addition of aqueous solution (100 ml) of 3-{[2-(methylsulfonyl)hydrazinyl]carbonyl}-1-[2-oxo-2-(thiophen-2-yl)ethyl]pyridinium chloride (10 gm) at RT. Reaction mixture was stirred for 1 hour and water (300 ml) was added and further stirred for one hour at RT. The separated solid was filtered and dried to give title compound (6.1 gm) as solid.

(Method C)

To a stirred solution of sodium decanoate (5.1 gm) in water (50 ml), solution of 3-{[2-(methylsulfonyl)hydrazinyl]carbonyl}-1-[2-oxo-2-(thiophen-2-yl)ethyl]pyridinium chloride (10 gm,) in water (100 ml) was added at RT and stirred for 1 hour. The separated solid was filtered, washed with water (100 ml) and dried to give title compound (5.4 gm) as solid.

(Method D)

To a stirred solution of 3-{[2-(methylsulfonyl)hydrazinyl]carbonyl}-1-[2-oxo-2-(thiophen-2-yl)ethyl]pyridinium chloride (5 gm) in water (50 ml) was added triethylamine (1.5 ml) at RT. After 30 minutes stirring n-decanoic acid (2.28 gm) was charged at RT. Reaction mass was stirred for 1-2 hrs at RT. The obtained solid was filtered, washed with water (50 ml×2) and dried to get title compound (4.6 gm) as solid. Resulted solid was stirred in n-heptane (23 ml) at RT for 30 minutes, filtered, washed with n-heptane (5 ml) and dried to give title compound (3 gm) as solid (Method E)

To a stirred suspension of n-decanoic acid (45.8 gm) in water (600 ml) was added aqueous solution (400 ml) of sodium hydroxide (10.6 gm), followed by addition of aqueous solution (2000 ml) of 3-{[2-(methylsulfonyl)hydrazinyl]carbonyl}-1-[2-oxo-2-(thiophen-2-yl)ethyl]pyridinium chloride (100 gm) at RT and stirred for 1 hour. The separated solid was filtered, washed with water (2000 ml), and suck dried. Suck dried solid was dried in fluid bed dryer to yield the title compound (47.30 gm) as solid with HPLC purity more than 99%.

Compound 1 as obtained above is characterized as:

¹H NMR (DMSO-d₆, 400 MHz, ppm): 0.839-0.872 (6H, multiplet), 1.242 (24H, multiplet), 1.460-1.493 (4H, multiplet), 2.157-2.194 (4H, triplet), 2.896-2.922 (1H, multiplet), 6.452 (2H, broad multiplet), 7.336 (1H, broad multiplet), 8.064-8.211 (3H, broad multiplet), 8.890 (2H, broad multiplet), 9.439 (1H, broad multiplet)

IR (KBr): 2924 cm⁻¹, 2853 cm⁻¹, 1679 cm⁻¹, 1336 cm⁻¹

Example 2

Step (a): 3-{[2-(methylsulfonyl)hydrazinyl]carbonyl}-1-[2-oxo-2-(thiophen-2-yl)ethyl]pyridinium bromide Compound was prepared similarly as described in step-e of example-1 using 2-Bromo-1-(thiophen-2-yl) ethanone.

Step (b): Compound no 1

(Method A)

To a stirred solution of 3-{[2-(methylsulfonyl)hydrazinyl]carbonyl}-1-[2-oxo-2-(thiophen-2-yl)ethyl]pyridinium bromide (100.0 gm) in water (800 ml) was added saturated aqueous solution of sodium bicarbonate at 10-25° C. to achieve pH 7.0.5-7.5 and stirred for 2.5-3 hour. The separated solid was filtered, washed with water and dried. Dried solid was further stirred in hot water, filter and dried to give 3-{[2-(methylsulfonyl)hydrazinyl]carbonyl}-1-[2-oxo-2-(thiophen-2-yl)ethyl]pyridinium ylide as orange solid. To a stirred suspension of 3-{[2-(methylsulfonyl)hydrazinyl]carbonyl}-1-[2-oxo-2-(thiophen-2-yl)ethyl]pyridinium ylide (5 gm) in water (50 ml), decanoic acid (5.1 gm) in water (25 ml) was added. The reaction mixture was stirred for 0.5-1.0 hour at 50-60° C. The reaction mixture was cooled to RT and stirred for 10-12 hour. The separated solid was filtered and dried to get title compound (10 gm) as solid.

(Method B)

To a stirred solution of 3-{[2-(methylsulfonyl)hydrazinyl]carbonyl}-1-[2-oxo-2-(thiophen-2-yl)ethyl]pyridinium bromide (100.0 gm) in water (800 ml) was added saturated aqueous solution of sodium bicarbonate at 10-25° C. to achieve pH 7.0.5-7.5 and stirred for 2.5-3 hour. The separated solid was filtered, washed with water and dried. Dried solid was further stirred in hot water, filter and dried to give 3-{[2-(methylsulfonyl)hydrazinyl]carbonyl}-1-[2-oxo-2-(thiophen-2-yl)ethyl]pyridinium ylide as orange solid. To a 3-{[2-(methylsulfonyl)hydrazinyl]carbonyl}-1-[2-oxo-2-(thiophen-2-yl)ethyl]pyridinium ylide (5 gm), added decanoic acid (5.1 gm,) and mixed well. The solid mixture was kept for 10-12 hours. The resulting solid (5 gm) was stirred in n-heptane (50 ml) for 1-1.5 hour at RT, filtered and dried to get title compound (6.4 gm) as solid.

Example 3: Preparation of Compound No 2

To a stirred suspension of octanoic acid (3.8 gm) in water (30 ml) was added aqueous solution (100 ml) of sodium hydroxide (1.05 gm), followed by aqueous solution (100 ml) of 3-{[2-(methylsulfonyl)hydrazinyl]carbonyl}-1-[2-oxo-2-(thiophen-2-yl)ethyl]pyridinium chloride as prepared in step (e) of example-1 (10 gm) at RT and stirred for 2 hour. The separated solid was filtered, washed with water and dried to give title compound (5.0 gm) as solid.

1H NMR (DMSO-d6 400 MHz ppm): 0.849-0.874 (3H, triplet), 1.247-1.249 (9H, doublet), 1.462-1.497 (2H, multiplet), 2.162-2.199 (2H, multiplet), 2.895-2.922 (1H, multiplet), 6.45-6.47 (1H, multiplet), 7.34-7.35 (1H, multiplet), 8.138-8.233 (2H, multiplet), 8.90 (1H, broad multiplet)

IR (KBr): 2924 $cm^{-1}$, 1676.79 $cm^{-1}$, 1334.4 $cm^{-1}$, 1156.7 $cm^{-1}$

Mass (m/z): 340 ($M^+$)

Pharmaceutical Compositions

In another embodiment present invention provides a pharmaceutical composition comprising a therapeutically effective amount of one or more of a compound of formula (I). While it is possible to administer therapeutically effective quantity of compounds of formula (I) either individually or in combination, directly without any formulation, it is common practice to administer the compounds in the form of pharmaceutical dosage forms comprising pharmaceutically acceptable excipient(s) and at least one active ingredient. These dosage forms may be administered by a variety of routes including oral, topical, transdermal, subcutaneous, intramuscular, intravenous, intreperitoneal, intranasal, pulmonary etc, preferably by oral route.

Oral compositions may be in the form of solid or liquid dosage form. Solid dosage form may comprise pellets, pouches, sachets or discrete units such as tablets, multiparticulate units, capsules (soft & hard gelatin) etc. Liquid dosage forms may be in the form of elixirs, suspensions, emulsions, solutions, syrups etc. Composition intended for oral use may be prepared according to any method known in the art for the manufacture of the composition and such pharmaceutical compositions may contain in addition to active ingredients, excipients as described in *Handbook of pharmaceutical excipients (sixth edition, 2009)* such as diluents, disintegrating agents, binders, solubilizers, lubricants, glidants, surfactants, suspending agents, pH adjusting agents, emulsifiers, chelating agents, stabilizers, flavours, sweeteners, colours etc.

Sterile compositions for injection can be formulated according to conventional pharmaceutical practice by dissolving or suspending the active substance in a vehicle such as water for injection.

The dosage form can have a slow, delayed or controlled release of active ingredients in addition to immediate release dosage forms.

The amount of active ingredient which is required to achieve a therapeutic effect will, of course, vary with the particular compound, the route of administration, the subject under treatment, and the particular disorder or disease being treated. The compounds of the invention may be administered by oral, inhalation or parenteral route at a dose of from 0.0005 to 100 mg/kg per day, preferably from 0.0005 to 50 mg/kg per day, more preferably from 0.001 to 20 mg/kg per day, most preferably from 0.1 to 50 mg/kg per day. The dose range for adult humans is generally from 100 mg per day to 2000 mg per day, preferably dose range is 150 mg per day to 1500 mg per day.

Compounds of present invention were found effective for the treatment of disease conditions associated with accumulation of AGE.

In another embodiment present invention provides method of treating disease condition selected from diabetes and aging related macrovascular and microvascular complications including heart failure, nephrological disorder, neuropathy, atherosclerosis, retinal disorder; dermatological disorder; endothelial or other organ dysfunction and growth impairment by administering a therapeutically effective amount of a compound of formula (I) to a mammal in need thereof.

Another embodiment of the present invention is the use of a compound of formula (I) for the preparation of a medicament for treating disease condition selected from diabetes and aging related macrovascular and microvascular complications including heart failure, nephrological disorder, neuropathy, atherosclerosis, retinal disorder; dermatological disorder; endothelial or other organ dysfunction and growth impairment.

Another embodiment of present invention provides pharmaceutical combination comprising compound of formula (I) and one or more therapeutic agent selected from a) antihypertensive agent; b) hypolipidemic agent; c) antidiabetic agent; d) antiplatelet agent; e) anti-thrombotic agent; f) antiobesity agent; g) agent for treatment of heart failure; and h) drug for diabetic vascular complications; i) agents for cardiovascular risk reduction; or a pharmaceutically acceptable salts thereof.

Another embodiment of present invention provides a method for treating disease condition selected from diabetes and aging related macrovascular and microvascular complications including heart failure, nephrological disorder, neuropathy, atherosclerosis, retinal disorder; dermatological disorder; endothelial or other organ dysfunction and growth impairment by administering a therapeutically effective amount of a compound of formula (I) and one or more therapeutic agent selected from a) antihypertensive agent; b) hypolipidemic agent; c) antidiabetic agent; d) antiplatelet agent; e) anti-thrombotic agent; f) antiobesity agent; g) agent for treatment of heart failure; and h) drug for diabetic vascular complications; i) agents for cardiovascular risk reduction; or a pharmaceutically acceptable salts thereof.

Another embodiment of present invention provides use of a compound of formula (I) and one or more therapeutic agent selected from a) antihypertensive agent; b) hypolipidemic agent; c) antidiabetic agent; d) antiplatelet agent; e) anti-thrombotic agent; f) antiobesity agent; g) agent for treatment of heart failure; and h) drug for diabetic vascular complications; i) agents for cardiovascular risk reduction; or a pharmaceutically acceptable salts thereof, for the preparation of a medicament for treating disease condition selected from diabetes and aging related macrovascular and microvascular complications including heart failure, nephrological disorder, neuropathy, atherosclerosis, retinal disorder; dermatological disorder; endothelial or other organ dysfunction and growth impairment.

The antihypertensive agent, as mentioned herein, includes but not limited to an angiotensin converting enzyme (ACE) inhibitor, a renin inhibitor, a beta adrenergic receptor blocker, an alpha adrenergic receptor blocker, a calcium channel blocker, a potassium channel activator, an aldosterone synthase inhibitor, a neutral endopeptidase (NEP) inhibitor, a dual angiotensin converting enzyme/neutral endopeptidase (ACE/NEP) inhibitor, an endothelin receptor antagonist, a dual angiotensin and endothelin receptor antagonist (DARA), a diuretic or a pharmaceutically acceptable salt thereof; the hypolipidemic agent or lipid-lowering agent as mentioned herein, includes but not limited to a MTP inhibitor, a HMG CoA reductase inhibitor, a squalene synthetase inhibitor, a fibric acid derivative, an ACAT inhibitor, a lipoxygenase inhibitor, a cholesterol absorption inhibitor, an ileal Na+/bile acid cotransporter inhibitor, an upregulator of LDL receptor activity, a cholesteryl ester transfer protein (CETP) inhibitor, a bile acid sequestrant, and/or nicotinic acid and derivatives or a pharmaceutically acceptable salt thereof; the antidiabetic agent, as mentioned herein, includes but not limited to a PPARγ agonist, a biguanide, a protein tyrosine phosphatase-1B (PTP-1B) inhibitor, a sulfonylurea, a meglitinide, an alpha glucoside hydrolase inhibitor, a PPARα agonist, a PPARδ agonist or antagonist, an alpha-amylase inhibitor, a fatty acid oxidation inhibitor, an A2 antagonist, a dipeptidyl peptidase IV (DP4) inhibitor, an aP2 inhibitor, a SGLT2 inhibitor, a glycogen phosphorylase inhibitor, a glucagon-like peptide-1 (GLP-1), an insulin or insulin mimetic, a PPAR.alpha./gamma dual agonist, an 11β-HSD 1 (11β-hydroxy-steroid dehydrogenase 1) inhibitor, other insulin sensitizing drug, a glucokinase activator, a VPAC2 receptor agonist or a pharmaceutically acceptable salt thereof; the antiplatelet agent as mentioned herein, includes but not limited to cyclooxygenase inhibitors, Adenosine diphosphate (ADP) receptor inhibitors, Phosphodiesterase inhibitors, Protease-activated receptor-1 (PAR-1) antagonists, Glycoprotein IIB/IIIA inhibitors, Adenosine reuptake inhibitors, Thromboxane inhibitors; the anti-thrombotic agent as mentioned herein, includes but not limited to melagatran and ximelagatran, warfarin and Factor Xa inhibitors such as rivaroxaban, apixaban, razaxaban or in each case, a pharmaceutically acceptable salt thereof; an agent useful for diabetic vascular complications in present invention includes without limitation aldose reductase inhibitor, AGE inhibitor or AGE breaker. Aldose reductase inhibitor, among those suitable for the treatment of diabetic complications, represent those which decrease intracellular sorbitols by inhibiting aldose reductases, and said sorbitols accumulate excessively by enhancement of a course of polyol metabolism which is induced by continuous hyperglycemia shown in tissues developing diabetic complication; the antiobesity agent, as mentioned herein, include but not limited to a 5HT (serotonin) transporter inhibitor, a NE (norepinephrine) transporter inhibitor, a CB-1 (cannabinoid-1 receptor) antagonist/inverse agonist, a ghrelin antibody, a ghrelin antagonist, a H3 (histamine H3) antagonist/inverse agonist, a NPY1 (neuropeptide Y Y1) antagonist, a NPY2 (neuropeptide Y Y2) agonist, a NPY5 (neuropeptide Y Y5) antagonist, leptin or its derivative, an opioid antagonist, an orexin antagonist, a BRS3 (bombesin receptor subtype 3) agonist, a CCK-A (cholecystokinin-A) agonist, a CNTF (ciliary neurotrophic factor), a CNTF derivative, a GHS (growth hormone secretagogue receptor) agonist, 5HT2c (serotonin receptor 2c) agonist, a Mc3r (melanocortin 3 receptor) agonist, a Mc4r (melanocortin 4 receptor) agonist, a monoamine reuptake inhibitor, a β3 (beta adrenergic receptor 3) agonist, a DGAT1 (diacylglycerol acyltransferase 1) inhibitor, a DGAT2 (diacylglycerol acyltransferase 2) inhibitor, a FAS (fatty acid synthase) inhibitor, a PDE (phosphodiesterase) inhibitor, a thyroid hormone β agonist, an UCP-1 (uncoupling protein 1), 2, or 3 activator, an acyl-estrogen, a glucocorticoid antagonist, a SCD-1 (stearoyl-CoA desaturase-1) inhibitor, a lipase inhibitor, a fatty acid transporter inhibitor, a dicarboxylate transporter inhibitor; agents for cardiovascular risk reduction, as mentioned herein, include but not limited to the compounds as disclosed in WO2007100295, which is cited herein as reference; or pharmaceutically acceptable salts thereof.

Preferably, said additional therapeutic agent is selected from metformin, glyburide, glipizide, gliclazide, acarbose, adiposine, camiglibose, emiglitate, miglitol, voglibose, glimepiride, rosiglitazone, pioglitazone, dapagliflozin, empagliflozin, canagliflozin, alogliptin, saxagliptin, linagliptin, sitagliptin, vildagliptin, amlodipine, felodipine, nicardipine, diltiazem, lercanidipine, captopril, benazepril, quinapril, fosinopril, ramipril, enalapril, lisinopril, perindopril, aliskiren, carvedilol, metoprolol, bisoprolol, atorvastatin, simvastatin, rosuvastatin, pravastatin, fluvastatin, cerivastatin, fenofibrate, gemfibrozil, clofibrate, bezafibrate, ciprofibrate, clinofibrate, probucol, ezetimibe, aliskiren, nicorandil, clopidogrel, prasugrel, aspirin, ticlopidine, hydrochlorothiazide, rivaroxaban, indapamide, trichlormethazide, altizide, chlorthalidone, furosemide, digitoxin, digoxin, spironolectone or its pharmaceutically acceptable salts thereof.

All aspects or embodiment of present invention, where appropriate (i.e. where compound of formula (I) is mentioned), apply equally to the compound of formula (II).

Biological Testing

Motor nerve conduction velocity evaluation was performed as a measure of AGE related diabetic complications.

In vivo study to evaluate effect of compound of present invention on Nerve Conduction Velocity Methods:

Induction of Diabetes Mellitus

Healthy male Wistar rats, 170-250 g, 6-10 weeks old, were selected for the study. The animals were divided into two groups i.e. a non-diabetic control group (Normal Control Rats) and a diabetic group. Diabetes was induced (in the diabetic group of animals) by a single intraperitoneal injection of streptozotocin (60 mg/kg body weight) dissolved in citrate buffer (pH 4.5) (Biro et al; *Brain Research Bulletin* (1997) 44(3): 259-263).

Treatment and Observation of Animals

Induction of diabetes was confirmed at one week after injection of streptozotocin by measuring the plasma glucose level. After 12 weeks of diabetes duration, the diabetic groups of animals were further subdivided into the following groups:

I. Diabetic control rats

II. Diabetic rats treated with compound No 1

150 mg/kg of Compound No 1 was administered to diabetic rats and diabetic control group was treated with vehicle for Compound 1. The rats were monitored throughout the experiment for water intake, food intake, changes in body weight, blood biochemistry parameters, urine parameters and mortality. The effects of 8 weeks of treatment on various parameters of the diabetic animals were compared with the untreated diabetic animals and the non-diabetic (Normal) control rats.

Nerve Conduction Velocity (NCV) Studies

After 8 weeks of treatment NCV was estimated as described by *Biro et al*, (1997). Briefly under anesthesia, the sciatic and tibial nerves were electrically stimulated at the sciatic notch or ankle, respectively. A supramaximal stimulus was delivered through needle electrodes, using a stimulator. Electromyograms (EMG's) from the plantar muscles were amplified and recorded using a data acquisition system (MacLab®, ADI instruments). Each EMG consists of two components: (1) the short latency direct motor response (M) and the monosynaptically elicited long-latency sensory response (H, Hoffmann reflex). Latency and the duration of the M responses were measured and the motor nerve conduction velocity (MNCV) was calculated.

The details of the recording and stimulating electrodes used for the study were as follows:

Recording Electrode: Small muscles of plantar surface of the hind foot were coated with jelly and then taped over the plantar surface with elastic of good width. Ground electrode was inserted under the skin of the heel.

Stimulating electrode: Stimulated nerve i.e. (a) sciatic (proximal) (b) tibial (distal) were present at the sciatic notch and at the ankle. Cathode was placed close to the nerve.

Anode was placed in proximity to the cathode. Upon stimulation of the nerve, responses (EMG) were recorded from the plantar surface. The NCV's of the treated rats in comparison to control (non diabetic) were studied.

Calculation:

$$MNCV = \frac{\text{Distance between the sciatic and tibial stimulation points}}{\text{Difference of the latency for } M_{sciatic} \text{ and } M_{tibial}}.$$

where

Latency: Time duration between the onset of the stimulus artifact to the peak of the first positive deflection of the muscle action potential.

Distance: The hind limb on which the recording was done, was fully stretched. The distance was measured using a thread between the two points where the cathode was inserted, both at the sciatic notch and at the ankle.

The percentage improvement in the nerve conduction velocity can be determined as follows % improvement in NCV=(Treated rat NCV−Diabetic rat NCV)×100/(Normal rat NCV−Diabetic rat NCV). One tailed t-test is used for the between treatment comparison.

Results: Diabetic animal showed impairment in NCV with respect to nondiabetic control animals. Compound 1 had shown improvement in NCV of diabetic animals as compared to diabetic control rats treated with vehicle, as shown in FIG. 1 (***p<0.001 Vehicle Vs Compound 1 by student's t-test).

The invention claimed is:

1. A process for preparing a Compound of Formula (I):

(I)

and isomers, stereoisomers, atropisomers, conformers and tautomers thereof; wherein, $Y^-$ is anion of Y;

Y is selected from nitric acid, $(C_2$-$C_{12})$alkyl sulfonic acid, $(C_3$-$C_{12})$cycloalkyl sulfonic acid, primary bile acids, secondary bile acids, conjugated bile acids, $CH_3$—$(CH_2)_z$—COOH, branched $(C_4$-$C_{14})$alkanecarboxylic acid, $(C_4$-$C_{14})$alkenecarboxylic acid, $(C_4$-$C_{14})$alkynecarboxylic acid and $C_3$-$C_{12}$ cycloalkanecarboxylic acid;

Z is selected from 1 to 14;
n is selected from 0 to 5;
$R^1$ is hydrogen;
$R^2$ is —$SO_2R^4$;
$R^3$ is heteroaryl; and
$R^4$ is $(C_1$-$C_8)$alkyl;
the process comprising,
reacting compound of formula (3a)

with Y or its pharmaceutically acceptable salt, optionally in presence of solvent or base or mixture thereof.

2. The process according to claim 1, wherein molar ratio of compound of formula (3a) and Y or its pharmaceutically acceptable salt is 6.0:0.5 to 0.5:6.0.

3. The process according to claim 2, wherein molar ratio of compound of formula (3a) and Y or its pharmaceutically acceptable salt is 1.0:1.0.

4. The process according to claim 1, wherein the compound of formula (3a) is 3-{[2-(methylsulfonyl)hydrazinyl]carbonyl}-1-[2-oxo-2-(thiophen-2-yl)ethyl]pyridinium and Y is $CH_3$—$(CH_2)_8$—COOH.

5. The process according to claim 1, wherein in the compound of Formula (I)

Y is $CH_3$—$(CH_2)_z$—COOH; $R^2$ is —$SO_2R^4$; $R^3$ is heteroaryl; Z is selected from 1 to 14 and $R^4$ is $(C_1$-$C_8)$ alkyl.

6. The process according to claim 1, wherein the compound of Formula (I) is selected from the group consisting of:

and

7. The process according to claim 1, wherein the compound of Formula (I) is

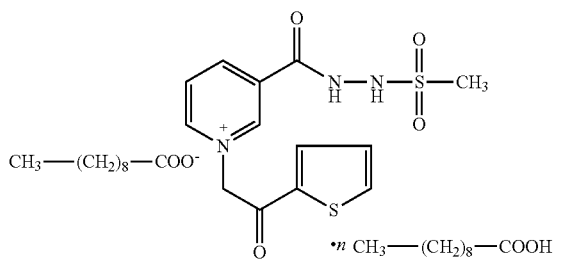

(II)

wherein n is 1 to 2.

8. A process for preparing Compound 1:

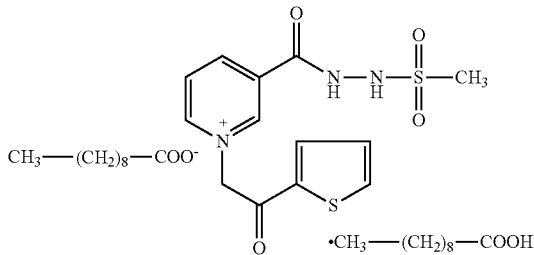

comprising, reacting 3-{[2-(methyl sulfonyl)hydrazinyl]carbonyl}-1-[2-oxo-2-(thiophen-2-yl)ethyl]pyridinium chloride with $CH_3$—$(CH_2)_8$—COOH or its alkaline metal salt or alkaline earth metal salt, in presence of solvent and optionally in presence of base;

wherein molar ratio of 3-{[2-(methylsulfonyl)hydrazinyl]carbonyl}-1-[2-oxo-2-(thiophen-2-yl)ethyl]pyridinium chloride to $CH_3$—$(CH_2)_8$—COOH or its alkaline metal salt or alkaline earth metal salt is 6.0:0.5 to 0.5:6.0.

* * * * *